United States Patent [19]
Mody et al.

[11] Patent Number: 5,639,327
[45] Date of Patent: Jun. 17, 1997

[54] DISPOSABLE DIAPER WITH THERMOPLASTIC MATERIAL ANCHORED HOOK FASTENER PORTION

[75] Inventors: Kirit C. Mody, Shoreview; Bernard D. Campbell, Fairmont, both of Minn.

[73] Assignee: Minnesota Mining and Manufacturing Company, St. Paul, Minn.

[21] Appl. No.: 823,390

[22] Filed: Jan. 21, 1992

Related U.S. Application Data

[62] Division of Ser. No. 438,693, Nov. 17, 1989, Pat. No. 5,100,400.

[51] Int. Cl.⁶ .................................................. B32B 7/14
[52] U.S. Cl. .......................... 156/148; 156/291; 156/305
[58] Field of Search ................................ 156/148, 291, 156/305, 244.11; 24/306, 422; 604/391, 389; 428/225, 257; 28/161

[56] References Cited

U.S. PATENT DOCUMENTS

| | | | |
|---|---|---|---|
| 3,138,841 | 6/1964 | Naimer | 264/157 |
| 3,320,649 | 5/1967 | Naimer | 28/161 |
| 3,537,946 | 11/1970 | Traux et al. | |
| 3,577,607 | 5/1971 | Ikoma et al. | 24/204 |
| 3,773,580 | 11/1973 | Provost | 156/66 |
| 3,849,840 | 11/1974 | Yamada et al. | |
| 3,940,525 | 2/1976 | Ballard | |
| 4,024,003 | 5/1977 | Bühler | 264/164 |
| 4,147,580 | 4/1979 | Buell | 156/291 |
| 4,410,327 | 10/1983 | Baggaley | |
| 4,454,183 | 6/1984 | Wollman | 24/306 |
| 4,568,342 | 2/1986 | Davis | |
| 4,973,326 | 11/1990 | Wood | 24/450 |

FOREIGN PATENT DOCUMENTS

| | | |
|---|---|---|
| 0211564 | 2/1987 | European Pat. Off. |
| 0258015 | 3/1988 | European Pat. Off. |
| 0278666 | 8/1988 | European Pat. Off. |
| 0319249 | 6/1989 | European Pat. Off. |
| 2101195 | 3/1972 | France |

*Primary Examiner*—Daniel Stemmer
*Attorney, Agent, or Firm*—Gary L. Griswold; Walter N. Kirn; William L. Huebsch

[57] ABSTRACT

A hook fastener portion for use in a hook and loop fastener that has a woven backing with portions of pile monofilaments projecting from its front surface providing hooks adapted for making releasable engagement with loops of the fastener. Only a layer of thermoplastic material along a rear surface of the backing and the mechanical engagement of the portions of the pile monofilaments woven into the backing anchor the monofilaments in the backing, and that layer of thermoplastic material can be a hot melt adhesive used to adhere the hook fastener portion to a substrate.

16 Claims, 3 Drawing Sheets

DISPOSABLE DIAPER WITH THERMOPLASTIC MATERIAL ANCHORED HOOK FASTENER PORTION

This is a division of application Ser. No. 07/438,693 filed Nov. 17, 1989, now U.S. Pat. No. 5,100,400.

TECHNICAL FIELD

The present invention relates to disposable diapers including hook and loop fasteners, and in particular to the hook portions of such fasteners.

BACKGROUND ART

Disposable diapers including hook and loop fasteners for fastening together portions of the diapers to secure them to individuals are well known in the art. U.S. Pat. Nos. 4,410,327 and 4,568,342 provide illustrative examples. Also it is well known to use hook fastener portions in such fasteners that have a woven backing and a plurality of pile monofilaments with portions woven into the backing and portions projecting from a front surface of the backing that have distal end portions adapted for releasable engagement with loops included in the fasteners (e.g., by forming arcuate hook portions or mushroom shaped heads at their ends), and a layer of adhesive along a rear surface of the backing adhering the hook fastener portions in place.

Heretofore, however, such woven hook fastener portions have been made in a continuous strip by a method including a weaving step to form the woven backing with portions of the pile monofilaments woven therein, a hook forming step in which arcuate hook portions or heads are formed on the projecting portions of the pile monofilaments, an autoclave step in which the woven fasteners are exposed to steam in an autoclave to shrink the backing, a binder coating step in which a coating of a liquid binder material for adhering together the warp and weft yarns and the woven in portions of the pile monofilaments is applied to the backing, and a drying step that takes about 48 hours in which the binding material on the backing is dried and cured; after which an adhesive for adhering the backing in place may be applied along the rear surface of the backing and the strip may be slit and/or cut to provide a hook fastener portion of a desired size for its intended application. While this method has produced a very suitable hook fastener portion which can withstand being opened and closed many times and being washed as is required for many uses, the number of steps it entails, and the batch nature of many of the steps it includes adds significantly to its cost. Thus, the hook fastener portion produced by that method is very high priced compared to hook fastener portions made by other methods such as continuous molding techniques that, while not of the high quality of the woven hook fastener portions made by the method described above, are still quite adequate for use in fasteners intended for certain uses, such as on disposable garments (e.g., disposable diapers) where a limited number of engagements and disengagements of the fasteners are anticipated.

DISCLOSURE OF INVENTION

The present invention provides a hook fastener portion with a woven backing that is significantly less expensive to make than the hook fastener portions with woven backings made by the method described above, and is quite adequate for use in fasteners intended for certain uses, such as on disposable garments (e.g., disposable diapers) where a limited number of engagements and disengagements of the fasteners are anticipated.

According to the present invention there is provided an inexpensive hook fastener portion adapted for use in hook and loop fastener means, such as on a disposable diaper of the type including a laminate having first and second opposite ends, and the hook and loop fastener means for fastening together portions of the laminate to secure the diaper to an individual including loop fastener portion means adjacent the first end of the laminate comprising a multiplicity of loops, and the hook fastener portion at the second end of the laminate. The hook fastener portion comprises a plurality of warp yarns, a plurality of weft yarns interwoven with the warp yarns to form with the warp yarns a woven backing having front and rear major surfaces, a plurality of pile monofilaments having portions woven into the backing and portions projecting from the front surface of the backing and having distal end portions adapted for making releasable engagement with the loops, and a layer of thermoplastic material along the rear surface of the backing. Only the layer of thermoplastic material and the mechanical engagement of the portions of the pile monofilaments woven into the backing with the warp and weft yarns anchor the monofilaments in the backing. Also, the layer of thermoplastic material can serve as or be a hot melt adhesive adapted to adhere the hook fastener portion to a substrate such as the laminate of the diaper.

Preferably the pile monofilaments are of larger diameter than the warp and weft yarns and include portions passing around weft yarns that protrude along the rear surface of the woven backing, and the layer of thermoplastic material is discontinuous and formed of discrete layer portions located around the protruding portions of the pile monofilaments and adhering the protruding portions of the pile monofilaments to adjacent portions of the warp and weft yarns.

When the hook fastener portion is intended to be attached to a polyethylene sheet included in the laminate of a disposable diaper, the layer of thermoplastic material is preferably an ethylene vinyl acetate hot melt adhesive weighing in the range of 2 to 12 grains per 4 inch by 6 inch area, and preferably weighing at least 4.5 grains per 4 inch by 6 inch area, with 5.5 grains per 4 inch by 6 inch area being a preferred weight which is selected as a compromise that provides both firm adhesion of the hook fastener portion to the layer of polyethylene, and low cost for the layer of hot melt adhesive. Such hook fastener portions can be easily attached to the polyethylene sheet using moderate pressure and conventional heat application or ultrasonic attaching techniques.

Also, when the hook fastener portion is intended to be used as part of the fastener for a disposable diaper, preferably the weft and warp yarns are of polyester (e.g., 150–34 denier polyester) and the pile monofilaments are of polypropylene (e.g., 0.004 to 0.010 inch diameter); and the backing of the hook fastener portion has in the range of 28 to 42 weft yarns crossing the warp yarns per inch of length of the warp yarns, with about 32 weft yarns crossing the warp yarns per inch of length of the warp yarns being preferred. It expected that such hook fastener portions having even lower numbers of weft yarns may be useful for certain purposes.

BRIEF DESCRIPTION OF DRAWING

The present invention will be further described with reference to the accompanying drawing wherein like reference numerals refer to like parts in the several views, and wherein.

DETAILED DESCRIPTION

Figure 1:
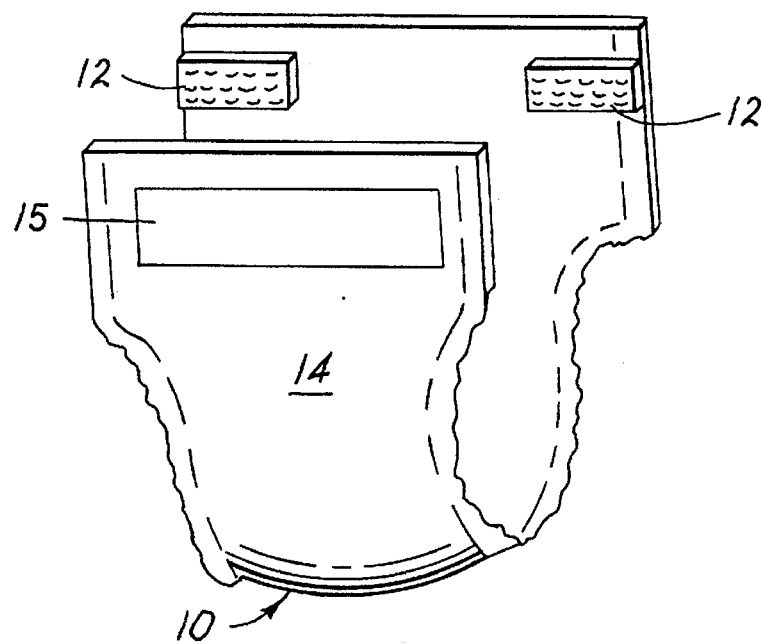
FIG. 1 is a perspective view of a disposable diaper including hook fastener portions according to the present invention.

Referring now to the drawing, there is shown in FIG. 1 a disposable diaper 10 including two hook fastener portions according to the present invention generally designated by the reference numeral 12.

Generally the disposable diaper 10 includes a laminate 14 having first and second opposite ends, and hook and loop fastener means for fastening together portions of the laminate 14 to secure the diaper 10 to an individual. The fastener means includes loop fastener portion means adjacent the first end of the laminate that could be provided by a portion of the laminate, but as illustrated comprises a loop fastener portion 15 adhered to the laminate 14 and having a multiplicity of loops projecting from its surface opposite the laminate 14; and the two spaced hook fastener portions 12 at the second end of the laminate 14.

Figure 2:
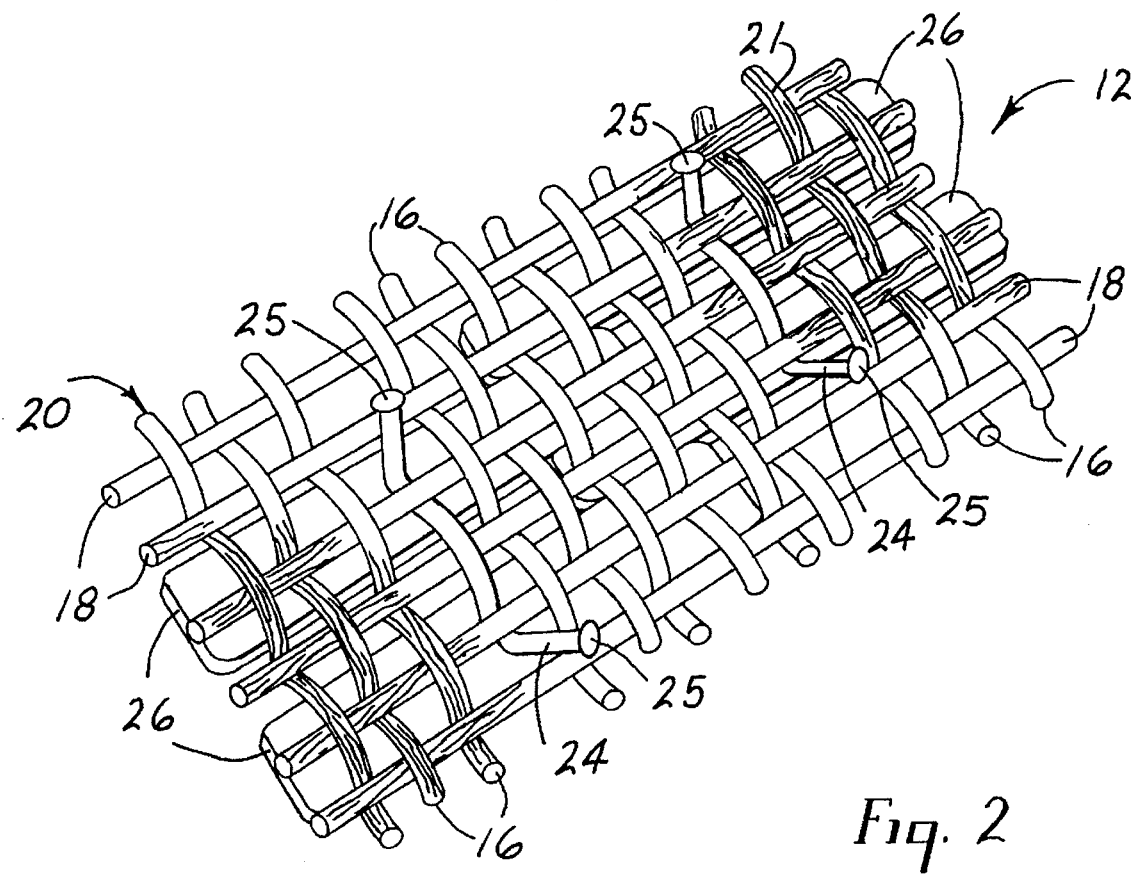
FIG. 2 is a much enlarged fragmentary perspective view of one of the hook fastener portions of FIG. 1 before it is attached to the diaper of FIG. 1.
Figure 3:
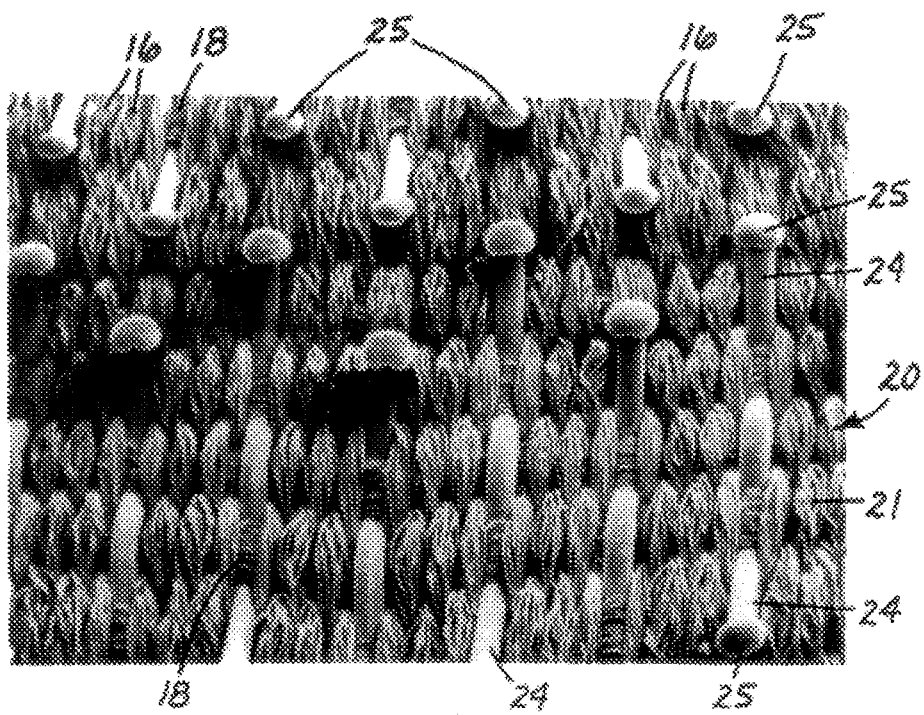
FIG. 3 is an enlarged photographic fragmentary top view of one of the hook fastener portions of FIG. 1 before it is attached to the diaper of FIG. 1.

As is best seen in FIGS. 2 and 3, the hook fastener portion 12 comprises a plurality of generally parallel warp yarns 16 (e.g., 156 warp yarns per inch), a plurality of generally parallel weft yarns 18 interwoven with the warp yarns 16 at right angles thereto (e.g., 28 to 42 and preferably 32 weft yarns per inch measured along the warp yarns) to form with the warp yarns a woven backing 20 having front and rear major surfaces 21 and 22, and a plurality of pile monofilaments 24 (e.g., twenty four 0.004 to 0.010 inch diameter polypropylene monofilaments 24 per inch of width measured along the weft yarns 18). The pile monofilaments 24 have portions woven in a "plane weave" manner shown in FIGS. 2, 3 and 4 into the backing 20, in which "plane weave" manner the woven in portions of the monofilaments 24 pass over 1 and under 2 weft yarns 18 and extend parallel to the warp yarns 16. The pile monofilaments 24 also include portions projecting from the front surface 21 of the backing and having generally semi cylindrical or mushroom shaped heads 25 at their distal ends (e.g., 112 to 168 and preferably 128 projecting portions per square inch). Also included in the hook fastener portion 12 is a discontinuous layer 26 of thermoplastic material along the rear surface 22 of the backing 20 with only the layer 26 of thermoplastic material and the mechanical engagement of the portions of the pile monofilaments 24 woven into the backing 20 around and intertwined with the warp and weft yarns 16 and 18 anchoring the pile monofilaments 24 in the backing 20, and the layer 26 of thermoplastic material also providing means for adhering the fastener portion 12 to the laminate 14.

Figure 4:
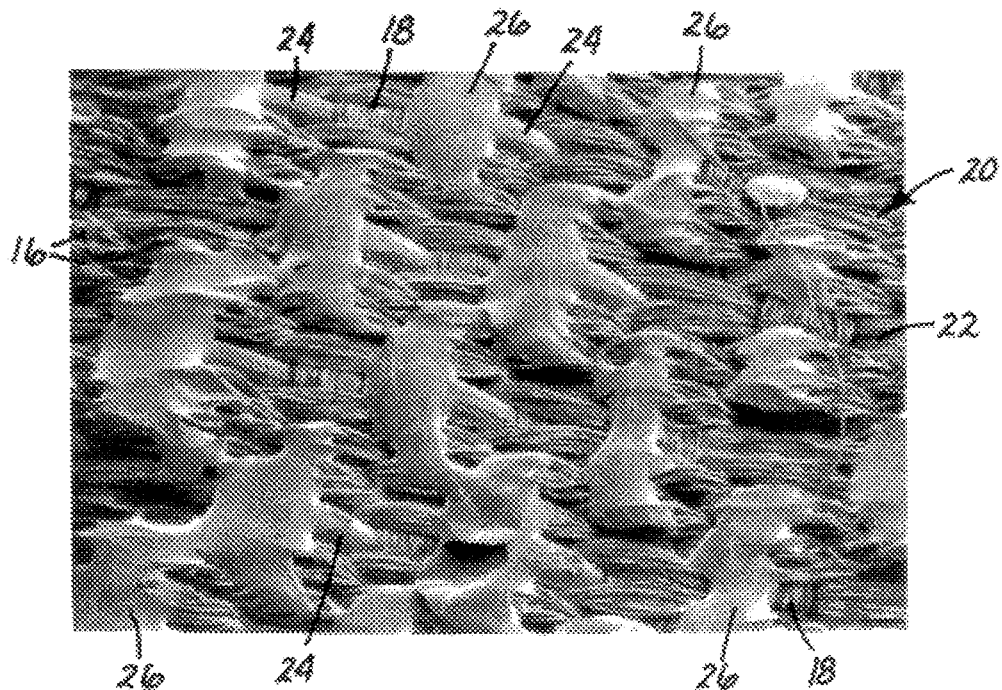
FIG. 4 is an enlarged photographic fragmentary bottom view of one of the hook fastener portions of FIG. 1 before it is attached to the diaper of FIG. 1.

As can best be seen in FIG. 4, the pile monofilaments 24 are of substantially larger diameter than the stranded warp and weft yarns 16 and 18 and include portions 27 passing around weft yarns 18 that protrude along the rear surface 22 of the woven backing 20 because of their larger diameter and stiffness and because they remain round while the yards can flatten as they pass around another yarn. The layer of thermoplastic material 26 is discontinuous and formed of discrete layer portions 28 that are located around the protruding portions 27 of the pile monofilaments 24 and adhere the protruding portions 27 of the pile monofilaments 24 to adjacent portions of the warp and weft yarns 16 and 18.

Although other thermoplastic materials such as "JET MELT" hot melt adhesives commercially designated 3762LM and 3792LM and available from Minnesota Mining and Manufacturing Company, St. Paul, Minn. or the hot melt adhesive commercially designated 7199D available from Bostic Division, Middleton, Mass., could be used as the layer 26 of thermoplastic material; a presently preferred thermoplastic material or hot melt adhesive described in U.S. Pat. No. 4,710,190 (the content whereof is incorporated herein by reference) consists of 60 percent by weight of an ethylene vinyl acetate adhesive (e.g., the adhesive commercially designated "Elvax 210" available from E. I. dupont deNemours and Company, Wilmington, Del., and 40 percent by weight of a suitable tackifyer (e.g., the tackifyer commercially designated "Piccolyte HM-90" available from Hercules Incorporated, Midwestern Region, Naperville, Ill., to which total weight of that mixture is added 1 percent of an antioxidant (e.g., the antioxidant commercially designated "Irganox 1010" available from Ciba-Geigy Corporation, Hawthorne, N.Y.

Figure 5:
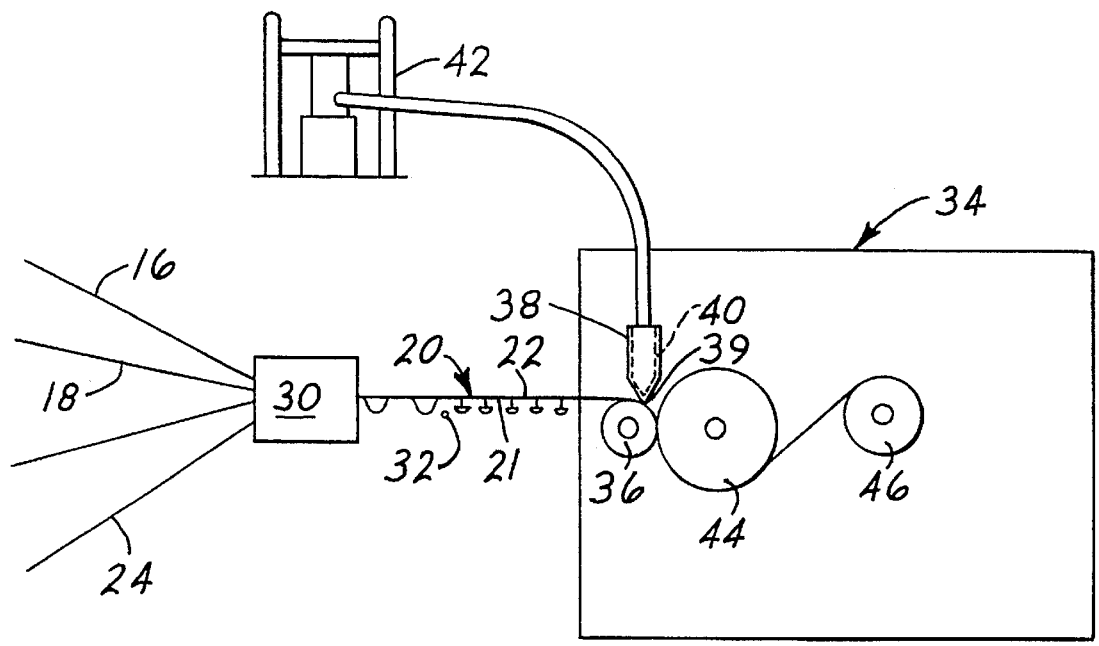
FIG. 5 is a schematic view of a method for making the hook fastener portions of FIG 1.

FIG. 5 illustrates a method according to the present invention for making the hook fastener portion 12. Generally, that method includes the well known steps of weaving the warp yarns 16, weft yarns 18, and pile monofilaments 24 together to form from the woven backing 20 with portions of the pile monofilaments 24 projecting from its front surface 21 using a weaving machine 30 (e.g., either a model NF 53/66 weaving machine available from Jacob Muller of America, Charlotte, N.C. which forms the projecting portions of the pile monofilaments 24 into loops projecting from the front surface 21 of the backing 20, or a model NB 40 machine also available from Jacob Muller of America which simultaneously forms two parallel backings 20 with separate sets of warp and weft yarns 16 and 18, and weaves portions of a single set of pile monofilaments 24 into both backings 20 in a plane weave manner with portions of those monofilaments extending at right angles to and between opposed front surfaces 21 of the backings 20); and heating the projecting portions of the pile monofilaments 24 to form the heads 25 on their distal ends. Such head 25 forming when the backing 20 is formed by the model NF 53/66 weaving machine described above and illustrated in FIG. 5 is done by heating the center of the loops with a heated wire 32 so that the loops each will separate into two projecting portions of the monofilament 24 each with a head 25 at its distal end; and such head 25 forming when the backing 20 is formed by the model NB 40 weaving machine described above is done by heating the central parts of the portions of the monofilaments 24 extending between the backings 20 with a heated wire so that each portion will separate into two projecting portions of the monofilament 24 (one projecting from each backing 20), each with a head 25 at its distal end. The method then includes the further step of coating a layer 26 of thermoplastic material or hot melt adhesive along the rear surface 22 of the backing 20 so that only the layer 26 of thermoplastic material and the mechanical engagement of the portions of the pile monofilaments 24 woven into the backing 20 with the warp and weft yarns 16 and 18 anchor the monofilaments 24 in the backing 20. This coating step is performed by passing the woven backing 20 with the headed portions of the pile monofilaments 24 through a hot melt coating device 34, (e.g., made using the Model GRO72X1 hot melt pump and die assembly available from Meltex Corporation, Peachtree City, Ga. 30269), which can advantageously be done as that structure leaves the weaving machine 30 so that the weaving, heating and coating steps described above are done continuously on the same production line.

Preferably, as illustrated, that hot melt coating device 34 comprises a rubber back up roll 36 around which the backing 20 passes with its front surface 21 adjacent the back up roll 36, and an extrusion die 38 having a guide surface 39 and an elongate slot 40 extending transversely the entire width of the backing 20 along the rear surface 22 of the backing 20 as the backing moves across the die 38. Thermoplastic material from which the layer 26 is formed is pumped to the die 38 and through the slot 40 from a heated pail unloading pump 42 included in the hot melt pump and die asembly at a rate related to the speed of movement of the backing 20 across the die 38. The portions 27 of the pile monofilaments 24 that protrude along the rear surface 22 of the backing 20 wipe away the thermoplastic material exiting from the outlet slot 40 of the die 38 and cause the layer 26 of thermoplastic material to be discontinuous and formed of the discrete layer portions 28 located around the protruding portions 27 of the pile monofilaments 24. From the die 38 the rear surface 22 of the backing 20 passes through a nip between the roller 36 and a silicone rubber coated first water cooled roller 44 and around the roller 44 so that the layer portions 28 cool, solidify, and adhere the protruding portions 27 of the pile monofilaments 24 to adjacent portions of the warp and weft yarns 16 and 18. The nipped rollers 36 and 44 engage the adhesive coated backing 20, and one of them is driven to move the backing 20 through the hot melt coating device 34. The front surface 21 of the adhesive coated backing 20 then passes around a silicone rubber surface of a second water cooled roller 46 after which it may be slit and cut to length (not shown) to provide a multiplicity of the hook fastener portions 12. Subsequently, the hook fastener portions 12 may be attached to the laminate 14 of a disposable diaper 10 through the application of heat and pressure.

The present invention has now been described with reference to one embodiment thereof. It will be apparent to those skilled in the art that many changes can be made in the embodiment described without departing from the scope of the present invention. Thus the scope of the present invention should not be limited to the structure described in this application, but only by structures described by the language of the claims and the equivalents of those structures.

We claim:

1. A method for making a hook fastener portion comprising the steps of weaving warp yarns, weft yarns, and pile monofilaments together to form from the warp and weft yarns and portions of the pile filaments a woven backing with front and rear major surfaces and portions of the pile monofilaments projecting from the front surface of the woven backing, said weaving step being done using pile monofilaments that are of larger diameter than the warp and weft yarns to provide portions of the pile monofilaments passing around weft yarns that protrude along the rear surface of the woven backing;

adapting the projecting portions of the pile monofilaments to make releasable engagement with loops; and coating a layer of thermoplastic material along the rear surface of the backing so that only the layer of thermoplastic material and the mechanical engagement of the portions of the pile monofilaments woven into the backing with the warp and weft yarns anchor the monofilaments in the backing, said coating step comprising:

providing a die having a generally planar guide surface and an elongate outlet opening through the guide surface, feeding the thermoplastic material at a predetermined rate through the outlet opening, and moving the rear surface of the woven backing along the guide surface and over the outlet opening at a predetermined rate of movement related to the rate of feeding of the thermoplastic material and with the outlet opening extending transverse to the direction of movement of the woven backing so that the protruding portions of the of the pile monofilaments wipe the thermoplastic material from the outlet opening and cause the layer of thermoplastic material to be discontinuous and formed of discrete layer portions located around the protruding portions of the pile monofilaments that adhere the protruding portions of the pile monofilaments to adjacent portions of the warp and weft yarns.

2. A method for making a hook fastener portion for use on a disposable garment and attaching the hook fastener portion to a substrate of the garment, said method comprising the steps of weaving warp yarns, weft yarns, and pile monofilaments together to form from the warp and weft yarns and portions of the pile filaments a woven backing with front and rear major surfaces and having generally in the range of 28 to 42 weft yarns crossing the warp yarns per inch of length of the warp yarns, and portions of the pile monofilaments projecting from the front surface of the woven backing, said weaving step being done using pile monofilaments that are of larger diameter than the warp and weft yarns to provide portions of the pile monofilaments passing around weft yarns that protrude along the rear surface of the woven backing;

adapting the projecting portions of the pile monofilaments to make releasable engagement with loops;

coating a layer of thermoplastic material along the rear surface of the backing so that only the layer of thermoplastic material and the mechanical engagement of the portions of the pile monofilaments woven into the backing with the warp and weft yarns anchor the monofilaments in the backing, said coating step comprising:

providing a die having a generally planar guide surface and an elongate outlet opening through the guide surface, feeding the thermoplastic material at a predetermined rate through the outlet opening, and moving the rear surface of the woven backing along the guide surface and over the outlet opening at a predetermined rate of movement related to the rate of feeding of the thermoplastic material and with the outlet opening extending transverse to the direction of movement of the woven backing so that the protruding portions of the of the pile monofilaments wipe the thermoplastic material from the outlet opening and cause the layer of thermoplastic material to be discontinuous and formed of discrete layer portions located around the protruding portions of the pile monofilaments that adhere the protruding portions of the pile monofilaments to adjacent portions of the warp and weft yarns; and applying heat and pressure to soften and adhere the coating of thermoplastic material to said substrate.

3. A method according to claim 2 wherein said weaving, heating and coating steps are done continuously on the same production line.

4. A method according to claim 2 wherein said coating step coats a layer of ethylene vinyl acetate adhesive weighing in the range of 2 to 12 grains per 4 inch by 6 inch area.

5. A method according to claim 2 wherein said weaving step weaves a backing having about 32 weft yarns crossing the warp yarns per inch of length of the warp yarns.

6. A method according to claim 5 wherein in said weaving step the pile monofilaments are of 250 to 600 denier polypropylene and the warp and weft yarns are of 150–34 denier polyester, and said coating step coats a layer of ethylene vinyl acetate adhesive that weighs at least 4.5 grains per 4 inch by 6 inch area.

7. A method according to claim 2 wherein said coating step coats a layer of ethylene vinyl acetate adhesive and weighs at least 4.5 grains per 4 inch by 6 inch area.

8. A method according to claim 2 wherein said coating step coats a layer of ethylene vinyl acetate adhesive that weighs in the range of 2 to 12 grains per 4 inch by 6 inch area.

9. A method according to claim 2 wherein said coating step coats a layer of ethylene vinyl acetate adhesive that weighs about 5.5 grains per 4 inch by 6 inch area.

10. A method for making a hook fastener portion for use on a disposable garment, said method comprising the steps of:

weaving warp yarns, weft yarns, and pile monofilaments together to form from the warp and weft yarns and portions of the pile filaments a woven backing with front and rear major surfaces and having generally in the range of 28 to 42 weft yarns crossing the warp yarns per inch of length of the warp yarns, and portions of the pile monofilaments projecting from the front surface of the woven backing, said weaving step being done using pile monofilaments that are of larger diameter than the warp and weft yarns to provide portions of the pile monofilaments passing around weft yarns that protrude along the rear surface of the woven backing;

adapting the projecting portions of the pile monofilaments to make releasable engagement with loops; and coating a layer of thermoplastic material along the rear surface of the backing so that only the layer of thermoplastic material and the mechanical engagement of the portions of the pile monofilaments woven into the backing with the warp and weft yarns anchor the monofilaments in the backing, said coating step comprising:

providing a die having a generally planar guide surface and an elongate outlet opening through the guide surface, feeding the thermoplastic material at a predetermined rate through the outlet opening, and moving the rear surface of the woven backing along the guide surface and over the outlet opening at a predetermined rate of movement related to the rate of feeding of the thermoplastic material and with the outlet opening extending transverse to the direction of movement of the woven backing so that the protruding portions of the of the pile monofilaments wipe the thermoplastic material from the outlet opening and cause the layer of thermoplastic material to be discontinuous and formed of discrete layer portions located around the protruding portions of the pile monofilaments that adhere the protruding portions of the pile monofilaments to adjacent portions of the warp and weft yarns; said weaving, heating and coating steps being done continuously on the same production line.

11. A method according to claim 10 wherein said coating step coats a layer of ethylene vinyl acetate adhesive weighing in the range of 2 to 12 grains per 4 inch by 6 inch area.

12. A method according to claim 10 wherein said weaving step weaves a backing having about 32 weft yarns crossing the warp yarns per inch of length of the warp yarns.

13. A method according to claim 12 wherein in said weaving step the pile monofilaments are of 250 to 600 denier polypropylene and the warp and weft yarns are of 150–34 denier polyester, and said coating step coats a layer of ethylene vinyl acetate adhesive that weighs at least 4.5 grains per 4 inch by 6 inch area.

14. A method according to claim 10 wherein said coating step coats a layer of ethylene vinyl acetate adhesive and weighs at least 4.5 grains per 4 inch by 6 inch area.

15. A method according to claim 10 wherein said coating step coats a layer of ethylene vinyl acetate adhesive that weighs in the range of 2 to 12 grains per 4 inch by 6 inch area.

16. A method according to claim 10 wherein said coating step coats a layer of ethylene vinyl acetate adhesive that weighs about 5.5 grains per 4 inch by 6 inch area.

* * * * *